United States Patent [19]

Stern

[11] 4,435,449
[45] Mar. 6, 1984

[54] TREATMENT OF MINIMAL BRAIN DYSFUNCTION (MBD)

[75] Inventor: Warren C. Stern, Raleigh, N.C.

[73] Assignee: Burroughs Wellcome Co., Research Triangle Park, N.C.

[21] Appl. No.: 395,147

[22] Filed: Jul. 6, 1982

Related U.S. Application Data

[63] Continuation of Ser. No. 263,717, May 14, 1981, abandoned.

[51] Int. Cl.$^3$ ............................................. A61K 31/135
[52] U.S. Cl. ...................................................... 424/330
[58] Field of Search ......................................... 424/330

[56] References Cited

U.S. PATENT DOCUMENTS 3,819,706  6/1974  Mehta ................................. 424/330
3,885,046  5/1975  Mehta ................................. 424/330

OTHER PUBLICATIONS

Stern, Chem. Abst., vol. 92, 1980-34480.
Canning et al., British J. of Pharmacology, (1979), 66, 104–105.
Communications, J. Pharm. Pharmac. (1977), 29, pp. 767–770.
Stern et al., Life Sciences, vol. 25, pp. 17–17–1724.
Whiteman et al., J. Clin. Psychiatry, (1982), Failure of Bupropion to Affect Prolactin or Growth Hormone.
Pharmacological and Biochemical Properties of Drug Substances, vol. 3, "Bupropion", R. A. Maxwell et al., Amer. Pharm. Ass. Academy of Pharm. Sciences–Publisher
Studies Concerning the Mechanism of the Antidepressant Activity of Bupropion, R. M. Ferris, J. Clin. Psychiatry (1982).
R. M. Ferris et al., Drug Development Research, 1:21–35, (1981).
Laakmann et al., Life Sciences, vol. 30, pp. 1725–1732.
Butz et al., Impess: Jour. of Exp. Pharm. & Therapeutics (1982), The Relationship Between Bupropion Disposition and Dopamine Uptake in Rats and Mice.
Neurochemical and Neuropharmacological Investigations into the Mechanisms of Action of Bupropion-HCl-A New Atypical Antidepressant Agent, Ferris et al., Typical and Atypical Antidepressants, Molecular Mechanisms, Raven Press, N.Y. (1982).

*Primary Examiner*—Stanley J. Friedman
*Attorney, Agent, or Firm*—Donald Brown

[57] ABSTRACT

A method of Treatment of Minimal Brain Dysfunction (MBD) also known as ATTENTION DEFICIT DISORDER in humans by the administration of the compound of the formula I

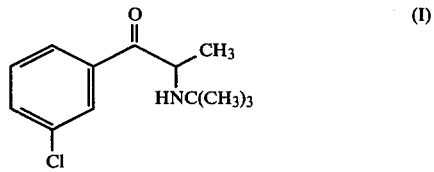

or a pharmaceutically acceptable acid addition salt thereof in a non-toxic, effective therapeutic amount (calculated as base) to a human in need thereof.

10 Claims, No Drawings

TREATMENT OF MINIMAL BRAIN DYSFUNCTION (MBD)

This is a continuation of application Ser. No. 263,717 filed May 14, 1981, now abandoned.

BACKGROUND OF THE INVENTION

This invention is directed to a method of Treatment of Minimal Brain Dysfunction in humans by the administration to the humans of the compound of the formula I

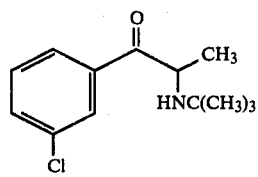

or a pharmaceutically acceptable acid addition salt thereof in a non-toxic, therapeutic amount (calculated as base) to a human in need thereof.

As used herein the term Minimal Brain Dysfunction is characterized by inattention, impulsively, with or without hyperactivity, usually with an onset before age 7 and a duration greater than six months. For further detail concerning the symptoms or diagnosis of minimal brain dysfunction also known as ATTENTION DEFICIT Disorder, see the Quick Reference to the Diagnostic Criteria from DSM-111, ©, The American Psychiatric Association, 1980, pp. 26 to 29 (314.01 and 314.80). Also, see Minimal Brain Dysfunction in Children, ©, John Wiley and Sons Inc., 1971 for additional information.

In U.S. Pat. Nos. 3,819,706 and 3,885,046, the compound of formula I (named m-chloro-$\alpha$-t-butylaminopropiophenone) and salts thereof were disclosed as being antidepressants.

The most common pharmacological treatment of MBD (this includes the childhood disorder of hyperactivity or hyperkinesis) is administration of stimulant drugs, such as methamphetamine, pemoline or methylphenidate. In the U.S.A., a few million children are treated annually for this disorder. While these drugs are effective in many cases they often cause a reduction in the growth of children and have an abuse liability. The drugs also tend exert sympathomimetic effects of increase in heart rate and blood pressure.

The compound or salts of formula I offers the advantages of exhibiting fewer of the aforementioned effects than occur with methamphetamine, pemoline and methylphenidate. In particular, the compound or salts of formula I does not reduce body growth, does not elevate blood pressure or pulse rate, and has a lower likelihood of producing drug dependence or drug abuse.

The compound of formula (I) (the active ingredient) of the pharmaceutically acceptable acid addition salt thereof is preferably administered in unit dosage form to the human being treated.

A pharmaceutical composition containing a compound of formula (I), or a pharmaceutically acceptable salt thereof, may be presented in discrete units such as tablets, capsules, ampules or suppositories, each containing an effective amount of the compound or salt for treatment of minimal brain dysfunction.

As an example, for the treatment of humans having minimal brain dysfunction the preferred unit dosage of a compound of formula (I) or an acid addition salt thereof (as the base) for oral administration, or administration as a suppositiory, is about 15 milligrams to 500 milligrams, preferably 15 milligrams to 300 milligrams, and the most preferred unit dosage is 25 milligrams to 75 milligrams per day, (t.i.d.), three times a day for a 20 to 40 kg child. Therapeutic (effective) dosage in humans is preferably 1 to 10 mg/kg (orally) per day in order to treat a patient. Treatment is given on a continuous basis to a person who had already been identified as having minimal brain dysfunction. All the above doses are given in terms of the weight of a compound of formula (I) in the form of its base, but as will be appreciated from the foregoing information, it may be administered in the form of a pharmaceutically acceptable acid addition salt thereof. Parenteral administration may be used and in this case the parenteral dose would be about ½ the oral dosage.

A compound of formula (I) or pharmaceutically acceptable salts thereof may be presented as an oral unit preparation (for example as a cachet, tablet or capsule) containing one or more pharmaceutically acceptable carriers which may take the form of solid diluents such as lactose, cornstarch, micronized silica gel as well as other excipients known in the art.

It should be understood that in addition to the aforementioned ingredients, the pharmaceutical composition of this invention may include one or more of additional ingredients e.g., pharmaceutically acceptable carriers such as diluents, buffers, flavouring agents, binders, surface active agents, thickeners, lubricants, preservatives, and the like. The formulations may be prepared by admixture of the ingredients, and, if necessary, shaping the resulting mass, and filling into suitable comtainers.

The compound used in this invention is preferably presented for use as a pharmaceutically acceptable acid addition salt. Examples of some of the pharmaceutically acceptable salts which can be utilized are salts of the following acids: hydrochloric, sulfuric, phosphoric and toluenesulphonic.

Reference should be had to U.S. Pat. Nos. 3,819,706 and 3,885,046, which are incorporated herein by reference hereto for a discription of the preparation of the compound of formula (I), acid addition salts thereof, tablets, capsules, parenteral solutions and suppositories incorporating same.

EXAMPLE I

The hydrochloride salt of formula I is administered as a tablet to a child who has been identified by a clinician as having the symptoms associated with minimal brain dysfunction. A child is orally administered a daily dose of 6 mg/kg (calculated as base) in three equally divided doses 6 hours between doses.

The child is treated continuously for several years and then taken off the drug periodically to determine if the underlying pathology is resolved. If not treatment is reinstituted. 180 mg is administered to 30 kg child daily.

EXAMPLE II

The procedure of Example 1 is followed however the hydrochloride salt at the same dosage is orally administered as an orange flavored aqueous solution, 1 teaspoon three times daily (60 mg base per spoonful).

I claim:

1. A method of treating minimal brain dysfunction in a human suffering from same, which comprises administering to said human an effective non-toxic minimal brain dysfunction amount of a compound of the formula (I)

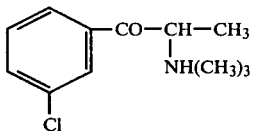

or a pharmaceutically acceptable acid addition salt thereof.

2. The method of claim 1 in which a pharmaceutically acceptable acid addition salt thereof is administered.

3. The method of claim 2 in which the salt is the hydrochloride salt.

4. The method of claim 1, 2 or 3 which the compound or salt is administered in a pharmaceutically acceptable carrier therefor.

5. The method of claim 1, 2, 3 or 4 in which the compound or salt is administered orally.

6. The method of claim 5 in which the compound or salt is administered in a pharmaceutically acceptable carrier therefor.

7. A method of treating minimal brain dysfunction in a human suffering from same, which comprises orally administering to said human an effective non-toxic minimal brain dysfunction treatment amount of a pharmaceutically acceptable acid addition salt of the compound of formula (I)

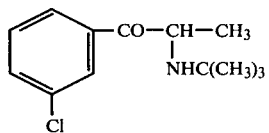

8. The method of claim 7 in which the salt is the hydrochloride salt.

9. The method of claim 7 or claim 8 in which the salt is administered in a pharmaceutically acceptable carrier therefor in the form of a tablet or capsule.

10. A method of treating minimal brain dysfunction in a human suffering from same, which comprises parenterally administering to said human a parenteral composition containing an effective non-toxic minimal brain dysfunction treatment amount of a pharmaceutically acceptable acid addition salt of the compound of formula I

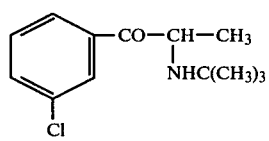

* * * * *

UNITED STATES PATENT AND TRADEMARK OFFICE
CERTIFICATE OF CORRECTION

PATENT NO. : 4,435,449
DATED : Mar. 6, 1984
INVENTOR(S) : Warren C. Stern

It is certified that error appears in the above—identified patent and that said Letters Patent is hereby corrected as shown below:

In the ABSTRACT: In formula I change "$HNC(CH_3)_3$" to --$NHC(CH_3)_3$--

Column 1, line 17: in formula I change "$HNC(CH_3)_3$" to --$NHC(CH_3)_3$--

Column 3, line 10: in formula I change "$NH(CH_3)_3$" to --$NHC(CH_3)_3$--

Signed and Sealed this

Eighth Day of January 1985

[SEAL]

Attest:

Attesting Officer

GERALD J. MOSSINGHOFF

Commissioner of Patents and Trademarks